United States Patent

Baba

[11] Patent Number: 5,905,658
[45] Date of Patent: May 18, 1999

[54] SIMULATION METHOD AND APPARATUS OF JAW MOVEMENT

[75] Inventor: Masami Baba, Saitama, Japan

[73] Assignee: Nikon Corporation, Tokyo, Japan

[21] Appl. No.: 08/813,082

[22] Filed: Mar. 7, 1997

[30] Foreign Application Priority Data

Mar. 7, 1996 [JP] Japan ................................. 8-049762

[51] Int. Cl.$^6$ ............................. G06F 17/50; A61C 11/00
[52] U.S. Cl. ............................................. 364/578; 433/69
[58] Field of Search ............................. 364/578; 433/69, 433/213

[56] References Cited

U.S. PATENT DOCUMENTS

| Re. 31,615 | 6/1984 | Lee | 433/73 |
| 3,896,550 | 7/1975 | Lee | 433/57 |
| 4,034,474 | 7/1977 | Lee | 433/69 |
| 4,045,872 | 9/1977 | Arant | 433/55 |
| 4,126,938 | 11/1978 | Lee | 433/69 |
| 4,189,837 | 2/1980 | Stele | 433/57 |
| 4,234,306 | 11/1980 | Hamada et al. | 433/55 |
| 4,270,901 | 6/1981 | Comparetto | 433/54 |
| 4,368,041 | 1/1983 | Roup | 433/69 |
| 4,417,873 | 11/1983 | Kulas | 433/57 |
| 4,843,497 | 6/1989 | Leyden | 360/79 |
| 5,108,292 | 4/1992 | Kirk et al. | 434/263 |
| 5,338,198 | 8/1994 | Wu et al. | 433/213 |
| 5,340,309 | 8/1994 | Robertson | 433/69 |

OTHER PUBLICATIONS

Siemens Aktiengesellschaft, Dental Division, Bensheim, W. Germany, "Sirognathograph", published 1992.

J. Jpn. Prosthodont. Soc., 31, pp. 805–818, 1987, "A Three Dimensional Study of the Retrusive Movement of the Mandible", Kiyoshi Koyano.

J. Jpn. Prosthodont. Soc., 37, pp. 159–171, 1993, "A Study on 3–dimensional Condylar Movements in Lateral Mandibular Movements", Miwa Tsukiyama et al.

*Primary Examiner*—Vincent N. Trans
*Attorney, Agent, or Firm*—Foley & Lardner

[57] ABSTRACT

A simulation method of jaw movement comprising:

a superimposing process step of reading dentition configuration data and jaw movement data, calculating a coordinate transformation matrix for matching a coordinate system of the dentition configuration data with a coordinate system in a jaw movement basic state in the jaw movement data, and transforming the dentition configuration data to coordinates on the coordinate system in the jaw movement basic state to obtain superimposed dentition configuration data; and a simulation process step of calculating superimposed dentition configuration data in another jaw movement state and superimposedly displaying a dentition configuration diagram obtained by converting the superimposed dentition configuration data to an image and a jaw movement state diagram obtained by converting the jaw movement data to an image.

10 Claims, 14 Drawing Sheets

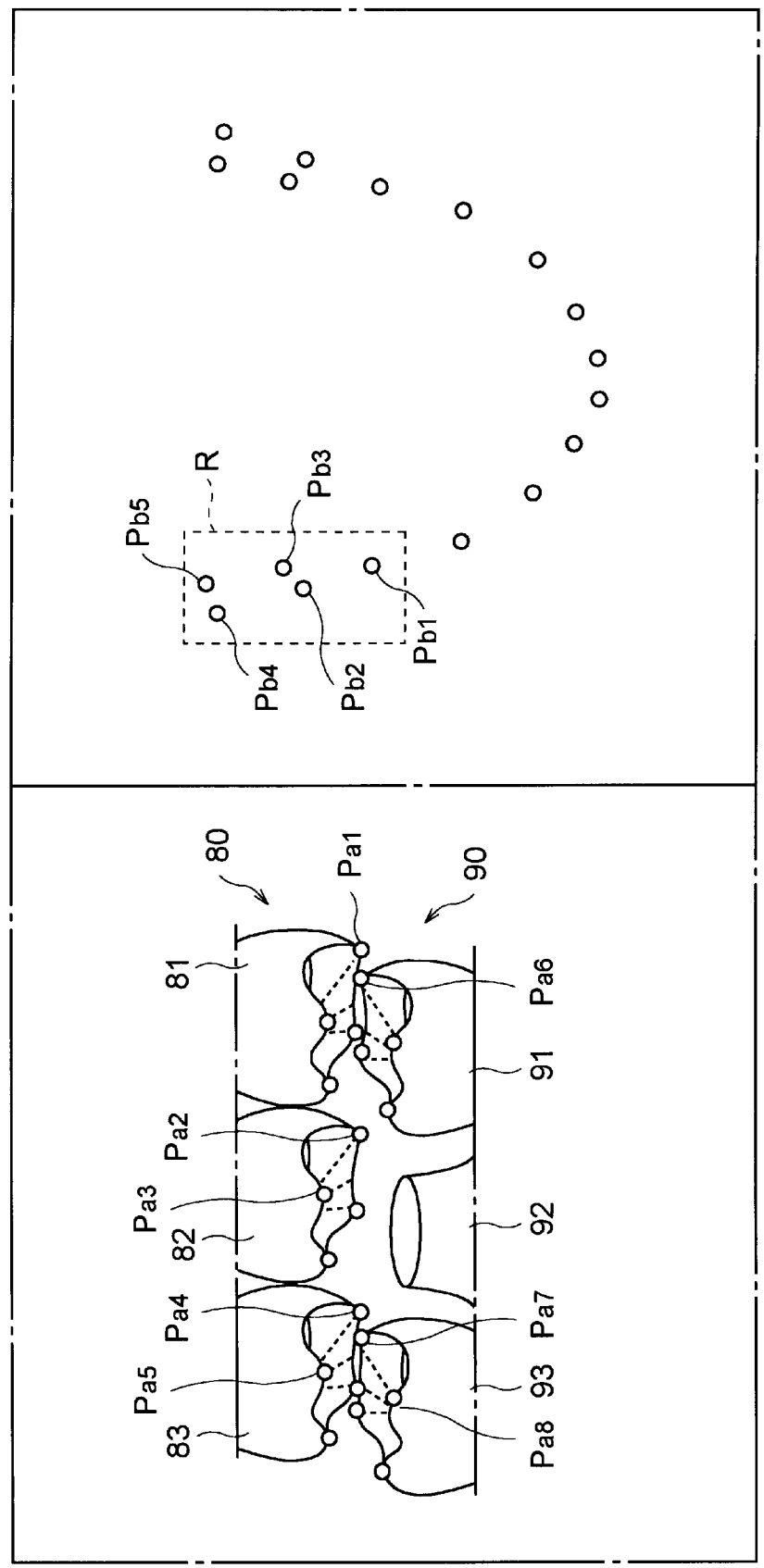

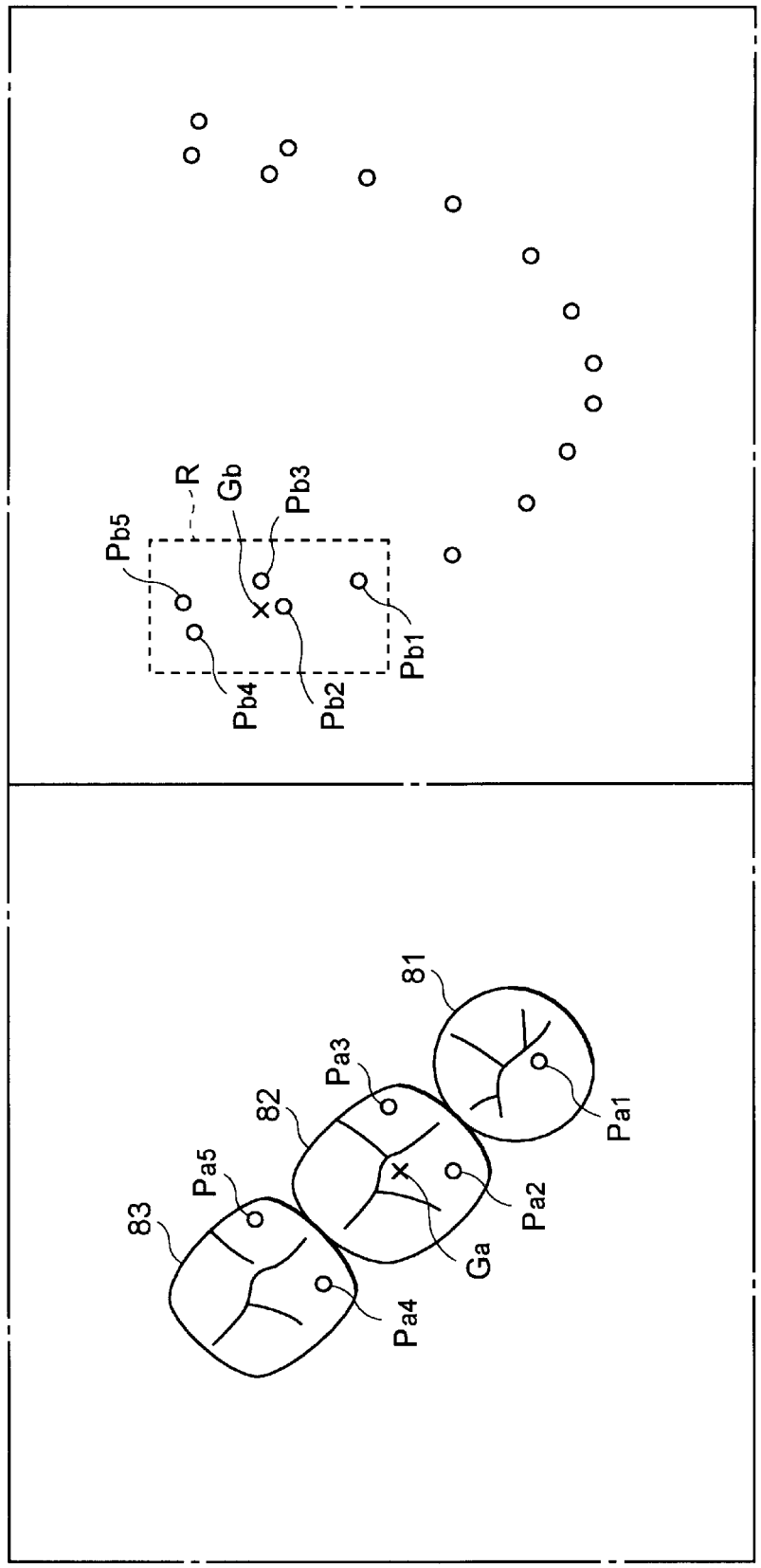

SIMULATION METHOD AND APPARATUS OF JAW MOVEMENT

BACKGROUND OF THE INVENTION

1. Field of the Invention

The present invention relates to a simulation method and apparatus of jaw movement. More particularly, the present invention relates to a simulation method of jaw movement and an apparatus therefor that can be used for designing a dental prosthesis or the like with a computer.

2. Related Background Art

In recent years there are proposed methods for designing the dental prosthesis by CAD/CAM or the like, i.e., by using a computer. This method is arranged to measure a configuration of a dentition of jaw including a portion on which a prosthesis is to be mounted and to design a configuration of the prosthesis on the computer, based on the measurement data. In the case of such designing of prosthesis, it is the simplest way to design the prosthesis (crown, bridge, or the like) in consideration of the relation with adjacent and pairing teeth in the occlusal relation at the intercuspal position (centric occlusal position). This method, however, could cause a feeling of disorder during mastication, because it excludes consideration on a change in the relative positional relation between jaw dentitions under masticating motion.

In order to overcome such a problem, it is desired to simulate motion of jaw, use the simulation result for designing, and design the prosthesis in consideration of the motion of jaw. For this purpose, a demand exists for a simulation method as accurate and easy as possible.

Under such circumstances many attempts have been made heretofore to achieve simulation of jaw motion. Examples of such simulation include a method for capturing a three-dimensional configuration of dentition into the computer, giving quantities of movement step by step under conditions considered by a human, and continuously moving the dentitions by connecting the quantities of motion, a method of line representation for connecting the motion data step from step, a method without use of computer, for mounting a gypsum cast on an occluding device and observing motion thereof on the occluding device, and so on. However, these conventional simulation methods required a lot of labor and time for data input and execution of simulation, which was a problem for many of them in being put into practical use. In addition, the accuracy and process time thereof were not satisfactory.

SUMMARY OF THE INVENTION

Under the above circumstances, an object of the present invention is to provide a simulation method and apparatus of jaw movement that can realize motion simulation most suitable for actual jaw movement of dentition or residual ridge in a computer and that is optimal for designing of dental prosthesis.

A simulation method of jaw movement according to the present invention comprises:

- a superimposing process step of reading dentition configuration data out of a dentition configuration data file storing dentition configuration data indicating a three-dimensional configuration of a dentition or a residual ridge and reading jaw movement data out of a jaw movement data file storing jaw movement data indicating loci of movement of plural jaw movement measurement points on the dentition or the residual ridge with jaw movement, calculating a coordinate transformation matrix for matching a coordinate system of said dentition configuration data with a coordinate system in a jaw movement basic state in said jaw movement data, and transforming said dentition configuration data to coordinates on the coordinate system in said jaw movement basic state using the coordinate transformation matrix to obtain superimposed dentition configuration data; and

- a simulation process step of, based on said jaw movement data and said superimposed dentition configuration data, calculating superimposed dentition configuration data in another jaw movement state and superimposedly displaying a dentition configuration diagram obtained by converting said superimposed dentition configuration data to an image and a jaw movement state diagram obtained by converting said jaw movement data to an image.

Also, the simulation method of the present invention may further comprise:

- a dentition configuration measuring step of measuring a three-dimensional configuration of a dentition or a residual ridge of a subject to obtain dentition configuration data thereof and storing the dentition configuration data obtained in said dentition configuration data file;

and/or

- a jaw movement measuring step of measuring loci of movement of plural jaw movement measurement points on a dentition or a residual ridge with jaw movement of a subject to obtain jaw movement data thereof and storing the jaw movement data obtained in said jaw movement data file.

This simulation method is arranged to measure how an arbitrary number of measurement points such as cuspid apexes of tooth bud move with mastication of a subject and to measure a three-dimensional configuration of a jaw dentition of the subject in a stationary state, thereby enabling easy simulation of movement of the jaw dentition with jaw movement of the subject on the computer using these measurement data.

It is also possible to retrieve jaw movement data suiting the subject at that time from the data preliminarily stored in a database section (jaw movement data file), instead of actually measuring the loci of movement of these points, and to simulate the jaw movement using the jaw movement data thus retrieved, which can further reduce a load on the subject during data measurement.

Namely, the simulation method of the present invention may be arranged in such a manner that jaw movement data of plural men is stored in said jaw movement data file and jaw movement data about a dentition or a residual ridge similar to the dentition or the residual ridge of the subject is read out of said jaw movement data file as being selected from said jaw movement data of plural men.

The arbitrary number of measurement points of the dentition or the residual ridge used in the jaw movement measuring step may be characteristic, morphological points of tooth bud such as the cuspid apexes or marks attached thereonto upon measurement. In this case, points corresponding to these plural measurement points are desirably included in the three-dimensionally measured data in the dentition configuration measuring step. This allows calculation of a transformation matrix for matching coordinates of the jaw movement data and dentition configuration data with each other, based on the jaw movement data in the predetermined jaw moving state (or in the basic state) of these plural measurement points measured in the jaw movement measuring step and the points corresponding to these plural measurement points in the dentition configuration data measured in the dentition configuration measuring step.

Namely, the simulation method of the present invention is preferably arranged in such a manner that said superimposing process step comprises:

- a step of reading the dentition configuration data out of the dentition configuration data file storing the dentition configuration data indicating the three-dimensional configuration of the dentition or the residual ridge and reading the jaw movement data out of the jaw movement data file storing the jaw movement data indicating the loci of movement of the plural jaw movement measurement points on the dentition or the residual ridge with jaw movement;
- a step of displaying a dentition configuration diagram obtained by converting said dentition configuration data to an image and a jaw movement state diagram obtained by converting the jaw movement data in the jaw movement basic state to an image and selecting jaw movement measurement points in said jaw movement state diagram and dentition configuration measurement points corresponding thereto in said dentition configuration diagram;
- a step of calculating a center of gravity of said dentition configuration measurement points and a center of gravity of said jaw movement measurement points;
- a step of calculating a function of a dentition configuration moment axis to minimize moments of said dentition configuration measurement points and a function of a jaw movement moment axis to minimize moments of said jaw movement measurement points;
- a step of correcting said dentition configuration measurement points so as to parallel said dentition configuration moment axis with said jaw movement moment axis to obtain corrected dentition configuration measurement points and calculating distribution area widths of respective three-dimensional coordinates of said corrected dentition configuration measurement points and distribution area widths of respective three-dimensional coordinates of said jaw movement measurement points;
- a step of calculating a translation matrix for matching the center of gravity of said dentition configuration measurement points with the center of gravity of said jaw movement measurement points;
- a step of calculating a rotation matrix for matching said dentition configuration moment axis with said jaw movement moment axis;
- a step of calculating a scaling matrix for matching the distribution area widths of said corrected dentition configuration measurement points with the distribution area widths of said jaw movement measurement points; and
- a step of transforming said dentition configuration data to coordinates on the coordinate system in said jaw movement basic state using a coordinate transformation matrix comprised of said translation matrix, said rotation matrix, and said scaling matrix to obtain superimposed dentition configuration data.

A simulation apparatus of jaw movement according to the present invention comprises:

- a storage device for storing a dentition configuration data file saving dentition configuration data indicating a three-dimensional configuration of dentition or a residual ridge and a jaw movement data file saving jaw movement data indicating loci of movement of plural jaw movement measurement points on the dentition or the residual ridge with jaw movement;
- an input device;
- a display device;
- a superimposing process section for reading the dentition configuration data out of said dentition configuration data file and the jaw movement data out of said jaw movement data file, respectively, calculating a coordinate transformation matrix for matching a coordinate system of said dentition configuration data with a coordinate system in a jaw movement basic state in said jaw movement data, and transforming said dentition configuration data to coordinates on the coordinate system in said jaw movement basic state using the coordinate transformation matrix to obtain superimposed dentition configuration data; and
- a simulation process section for, based on said jaw movement data and said superimposed dentition configuration data, calculating superimposed dentition configuration data in another jaw movement state and superimposedly displaying a dentition configuration diagram obtained by converting said superimposed dentition configuration data to an image and a jaw movement state diagram obtained by converting said jaw movement data to an image on said display device.

Also, the simulation apparatus of the present invention may further comprise:

- a dentition configuration measuring device for measuring a three-dimensional configuration of a dentition or a residual ridge of a subject to obtain dentition configuration data and storing the dentition configuration data obtained in said dentition configuration data file;

and/or

- a jaw movement measuring device for measuring loci of movement of plural jaw movement measurement points on a dentition or a residual ridge with jaw movement of a subject to obtain jaw movement data and storing the jaw movement data obtained in said jaw movement data file.

On the other hand, the simulation apparatus of the present invention may be arranged in such a manner that jaw movement data of plural men is stored in said jaw movement data file and said superimposing process section reads jaw movement data about a dentition or a residual ridge similar to the dentition or the residual ridge of the subject out of said jaw movement data file as selecting it out of said jaw movement data of plural men.

Further, the simulation apparatus of the present invention is preferably arranged in such a manner that said superimposing process section comprises:

- a data reading process section for reading the dentition configuration data out of said dentition configuration data file and the jaw movement data out of said jaw movement data file, respectively:
- a measurement point selecting process section for displaying a dentition configuration diagram obtained by converting said dentition configuration data to an image and a jaw movement state diagram obtained by converting the jaw movement data in the jaw movement basic state to an image on said display device and for accepting selection of jaw movement measurement points in said jaw movement state diagram and dentition configuration measurement points corresponding thereto in said dentition configuration diagram through said input device;

a center-of-gravity calculating process section for calculating a center of gravity of said dentition configuration measurement points and a center of gravity of said jaw movement measurement points;

a moment axis calculating process section for calculating a function of a dentition configuration moment axis to minimize moments of said dentition configuration measurement points and a function of a jaw movement moment axis to minimize moments of said jaw movement measurement points;

a distribution area calculating process section for correcting said dentition configuration measurement points so as to parallel said dentition configuration moment axis with said jaw movement moment axis to obtain corrected dentition configuration measurement points and for calculating distribution area widths of respective three-dimensional coordinates of said corrected dentition configuration measurement points and distribution area widths of respective three-dimensional coordinates of said jaw movement measurement points;

a translation matrix calculating process section for calculating a translation matrix for matching the center of gravity of said dentition configuration measurement points with the center of gravity of said jaw movement measurement points;

a rotation matrix calculating process section for calculating a rotation matrix for matching said dentition configuration moment axis with said jaw movement moment axis;

a scaling matrix calculating process section for calculating a scaling matrix for matching the distribution area widths of said corrected dentition configuration measurement points with the distribution area widths of said jaw movement measurement points; and a dentition configuration data transforming process section for transforming said dentition configuration data to coordinates on the coordinate system in said jaw movement basic state using a coordinate transformation matrix comprised of said translation matrix, said rotation matrix, and said scaling matrix to obtain superimposed dentition configuration data.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 4A and FIG. 4B are a side view of dentition configuration and a plan view of jaw movement basic sate, respectively, displayed on a display in the measurement point selecting step;

FIG. 5A and FIG. 5B are a plan view of dentition configuration and a plan view of jaw movement basic state, respectively, displayed on the display in the center-of-gravity calculating step;

DETAILED DESCRIPTION OF THE PREFERRED EMBODIMENTS

Figure 1:
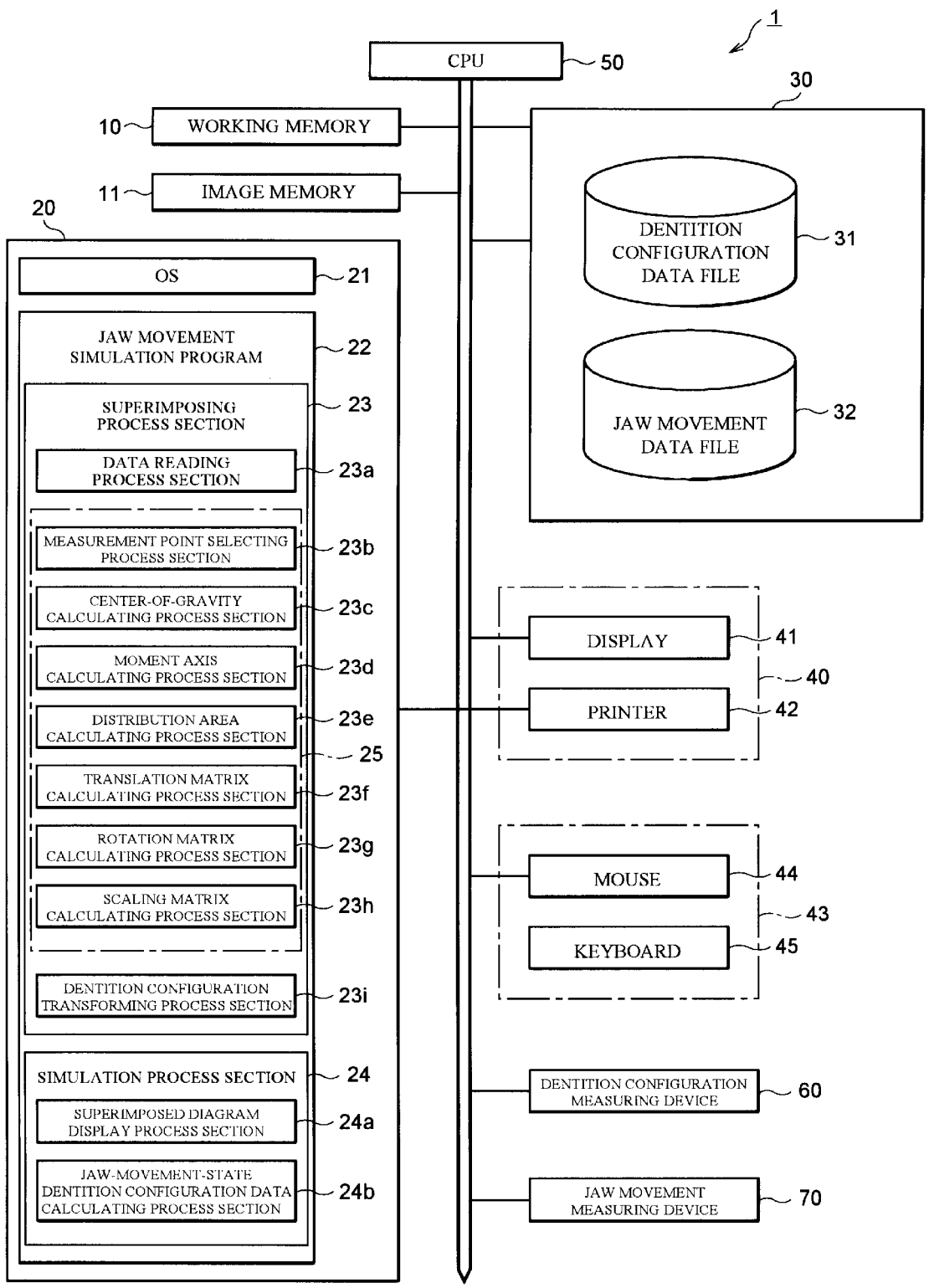
FIG. 1 is a block diagram to show an example of the jaw movement simulation apparatus according to the present invention.

The preferred embodiments of the present invention will be described with reference to the accompanying drawings. FIG. 1 is a block diagram to show an embodiment of the jaw movement simulation apparatus 1 according to the present invention. The simulation apparatus 1 of the present embodiment comprises a working memory 10 for temporarily storing data, an image memory 11 for storing image data, a first storage device 20 storing an operating system 21 and a jaw movement simulation program 22, a second storage device 30 storing a dentition configuration data file 31 and a jaw movement data file 32, a display 41 and a printer 42 as a display device 40, a mouse 44 and a keyboard 45 as an input device 43, and a CPU 50 for controlling execution of jaw movement simulation program 22 and the like.

The jaw movement simulation program 22 comprises a superimposing process section 23 for calculating a coordinate transformation matrix based on dentition configuration data and jaw movement data and transforming the dentition configuration data to coordinates on the coordinate system in the jaw movement basic state to obtain superimposed dentition configuration data, and a simulation process section 24 for calculating superimposed dentition configuration data in another jaw movement state based on the jaw movement data and the superimposed dentition configuration data and displaying a superimposed diagram of a dentition configuration diagram and a jaw movement state diagram on the display device 40. Further, the superimposing process section 23 comprises a data reading process section 23a, a measurement point selecting process section 23b, a center-of-gravity calculating process section 23c, a moment axis calculating process section 23d, a distribution area width calculating process section 23e, a translation matrix calculating process section 23f, a rotation matrix calculating process section 23g, a scaling matrix calculating process section 23h, and a dentition configuration data transforming process section 23i, wherein the process sections 23b to 23h compose a coordinate transformation matrix calculating process section 25. The simulation process section 24 comprises a superimposed diagram displaying process section 24a for displaying a superimposed image of dentition configuration diagram and jaw movement state diagram on the display device 40, and a jaw-movement-state dentition configuration data calculating process section 24b for calculating superimposed dentition configuration data in another jaw movement state based on the jaw movement data and the superimposed dentition configuration data. The contents of processes in the above various process sections will be described hereinafter in detail.

The dentition configuration data file 31 stores dentition configuration data to indicate a three-dimensional configuration of a dentition or a residual ridge of a subject in the form of three-dimensional coordinate data, while the jaw movement data file 32 stores jaw movement data to indicate loci of movement of a plurality of jaw movement measurement points on the dentition or the residual ridge with movement of jaw in the form of three-dimensional coordinate data. It is preferable that the jaw movement data file 32 also store the jaw movement data of the subject, but jaw movement data of plural men may be stored as database in the jaw movement data file. This permits us to use jaw movement data on a dentition or a residual ridge similar to the dentition or the residual ridge of the subject as selecting it from the jaw movement data of plural men.

Further, the simulation apparatus 1 of the present embodiment comprises a dentition configuration measuring device 60 and a jaw movement measuring device 70. The dentition configuration measuring device 60 is a three-dimensional measuring instrument for measuring a three-dimensional configuration of dentition or residual ridge of subject to obtain dentition configuration data as three-dimensional coordinate data and storing the dentition configuration data thus obtained in the dentition configuration data file 31. Such dentition configuration measuring device 60 may be either of a contact type or of a non-contact type, for example, Tristation (trade name) available from NIKON CORP.

Also, the jaw movement measuring device 70 is a three-dimensional displacement measuring system for measuring loci of movement of plural jaw movement measurement points on the dentition or residual ridge with jaw movement of subject to obtain jaw movement data as three-dimensional coordinate data and storing the jaw movement data thus obtained in the jaw movement data file 32. Specific examples of such jaw movement measuring device 70 include a system for using a measuring jig mounted on the maxilla and mandible of subject and measuring motion thereof, and a system for putting light emitting members on respective measurement points (cuspid apexes of dentition, for example) on the dentition or residual ridge of subject and photographing motion thereof by a CCD camera to obtain three-dimensional data thereof. For example, Kiyoshi Koyano, "A Three Dimensional Study of the Retrusive Movement of the Mandible" J. Jpn. Prosthedent Soc., 31: 805–818 (1987), describes the latter system and measuring method using it. This literature is incorporated as a reference in this specification.

Measurement by such dentition configuration measuring device 60 and jaw movement measuring device 70 is carried out, for example, as follows. Namely, first, a gypsum cast of dentition or residual ridge of subject is made in such a state that tooth buds or jaws of human are naturally closed, as called the intercuspal position or the centric occlusal position (in a preferable basic state). Another state may be employed as the basic state, but the intercuspal position or centric occlusal position is more preferable because of ease to measure.

Next, measurement of jaw movement including that in this basic state is carried out by the jaw movement measuring device 70. This measurement is carried out in such a way that a plurality of measurement points are determined at characteristic, morphological points of tooth bud, such as cuspid apexes or foveolae, at predetermined positions of residual ridge with marks attached to the mucous membrane, or the like and that loci of movement drawn by these measurement points with jaw movement are measured. The measurement of jaw movement is carried out preferably in the sequence of from the basic state (the state of intercuspal position) through the maximum opening position back to the initial state.

On the other hand, the gypsum cast made as described above is three-dimensionally measured by the dentition configuration measuring device 60 so that each measurement point used in this measurement of jaw movement can be identified clearly. The jaw movement data and dentition configuration data measured in this way is stored as database (data file) in memory areas of apparatus 1 in the form of three-dimensional coordinate data.

There is no specific restriction on a reference point or reference plane of the above three-dimensional coordinate data. For example, the center point between the left and right condylar tips may be employed as a reference point or the Camper plane may be employed as a reference horizontal plane.

An embodiment of the jaw movement simulation method according to the present invention is next explained with reference to the accompanying drawings. This method is carried out using the above-stated jaw movement simulation apparatus 1. In this example, the intercuspal position is used as the basic state for making the gypsum cast, and the cuspid apex of each tooth is used as a measurement point being a target. The intercuspal position means a state wherein the cuspid apexes of upper and lower dentitions occlude best, which is also called the centric occlusal position.

First, the jaw movement data and dentition three-dimensional configuration data is measured as follows in the measurement step.

(I) Measurement Step (i) Dentition configuration measuring step

A gypsum cast of dentition of the maxilla and mandible is made in the basic state. Then this gypsum cast is three-dimensionally measured by the three-dimensional measuring instrument (Tristation, for example) 60 while the gypsum cast is held so as to keep the positional relation of the maxilla and mandible including the cuspid apexes to obtain three-dimensional configuration (stereoscopic) data of dentition. The data thus obtained is stored in the dentition configuration data file 31.

(ii) Jaw movement measuring step

Taken with the jaw movement measuring device (the apparatus described in the foregoing literature, for example) 70 is (a) cuspid apex position data at the intercuspal position of the maxilla and mandible as to the whole jaws or as to part of jaws, and (b) cusp movement data of the mandible (the maxilla is fixed).

Although the data of (a) is part of the data of (b), it must be taken.

Specifically, light-emitting members are attached to the cuspid apexes of dentition of the maxilla and mandible and loci of movement thereof are photographed in plural directions through the CCD camera. Then image data obtained is binarized, the binary data is further converted to three-dimensional coordinate values to obtain jaw movement data, and the data obtained is stored in the jaw movement data file 32.

Figure 2:
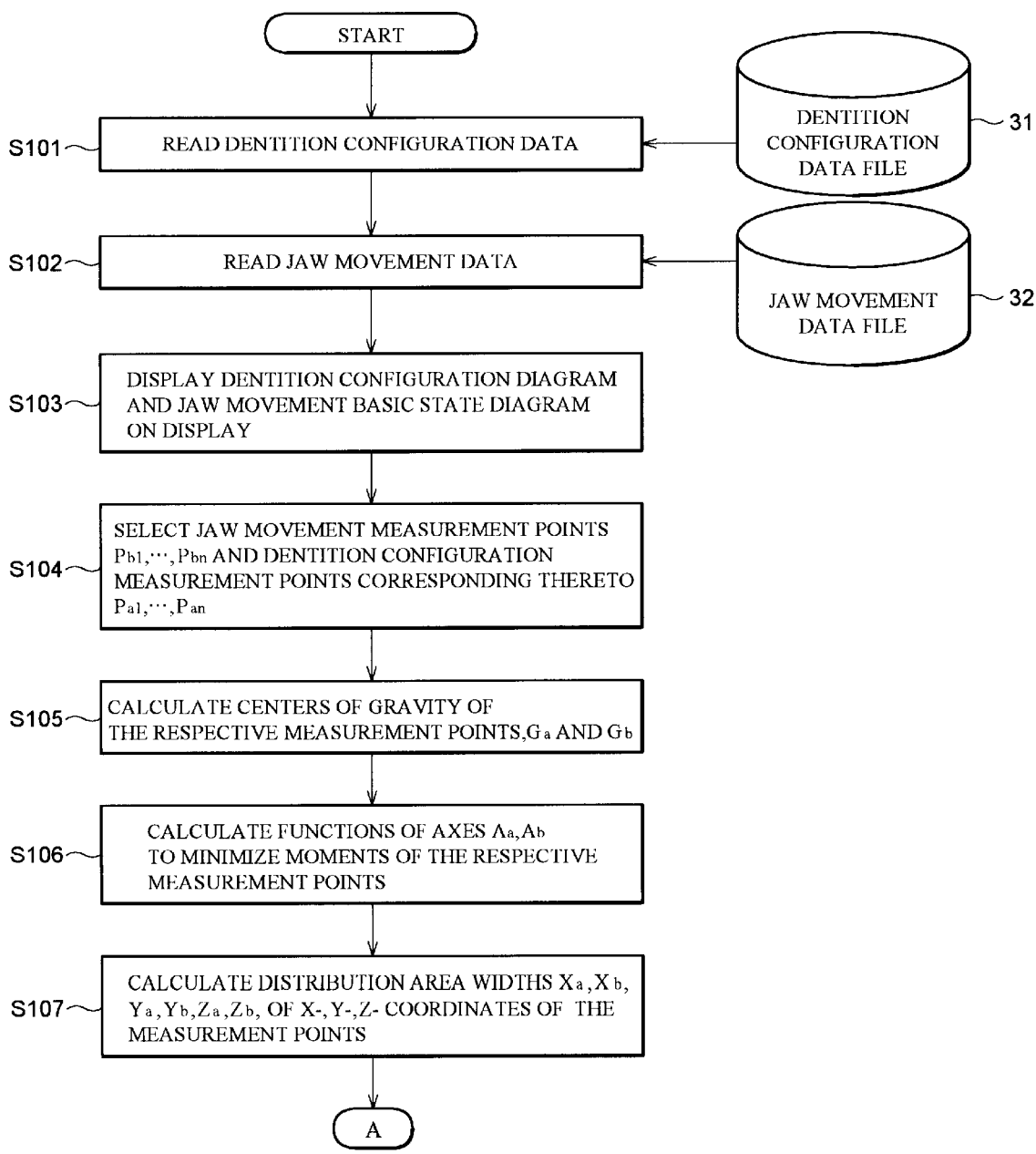
FIG. 2 is a flowchart to show an example of the jaw movement simulation program for carrying out the jaw movement simulation method according to the present invention.
Figure 3:
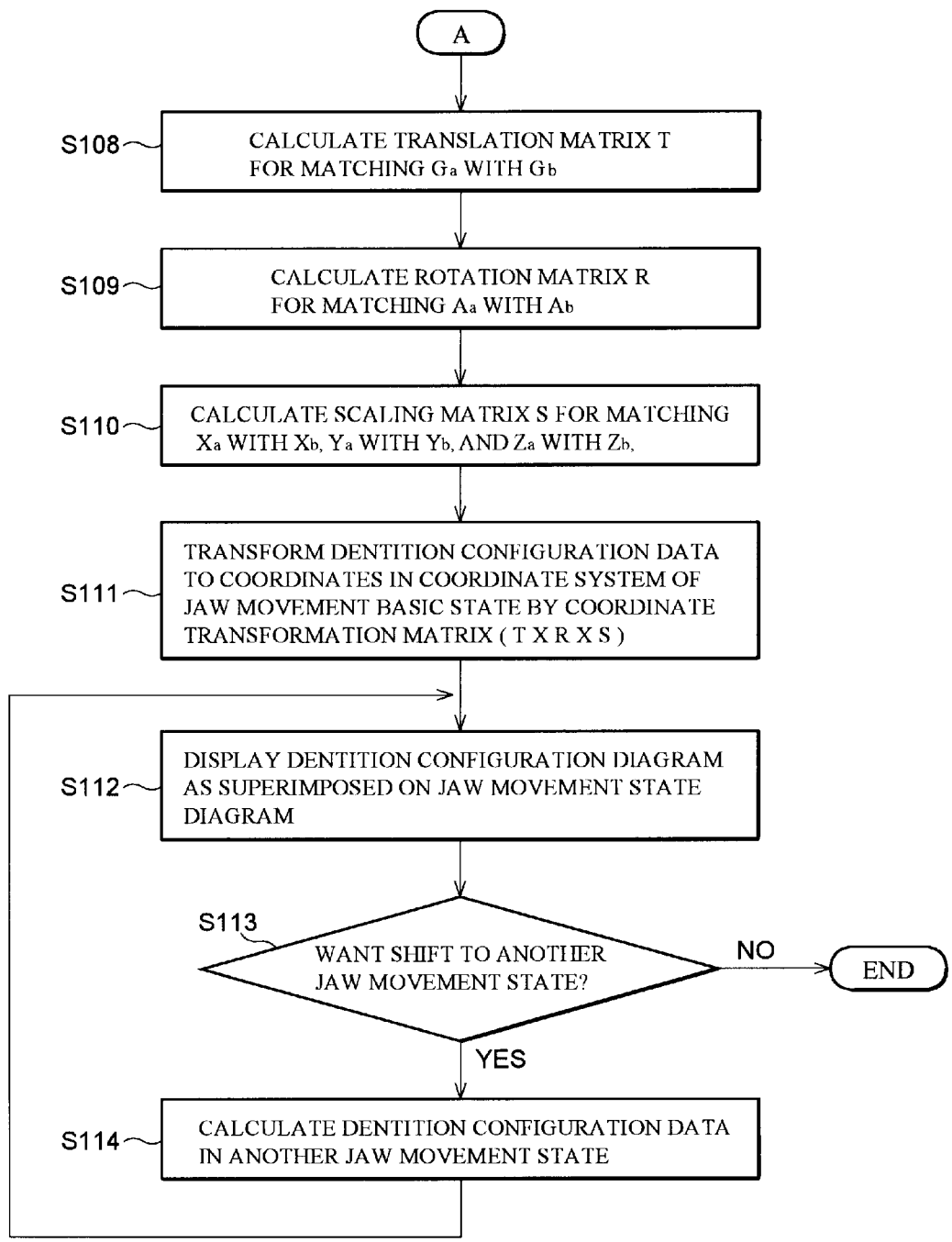
FIG. 3 is a flowchart to show an example of the jaw movement simulation program for carrying out the jaw movement simulation method according to the present invention.

Then the jaw movement simulation program 22 is started under control of OS 21 to execute the superimposing process step and simulation process step (see the flowchart shown in FIG. 2 and FIG. 3).

(II) Superimposing Process Step 23

(i) Data reading process step 23a

The dentition configuration data is read out of the dentition configuration data file 31 and the jaw movement data out of the jaw movement data file 32, respectively (S101, S102).

For the cases wherein the jaw movement data of subject does not exist in the jaw movement data file 32, the system may be arranged in such a manner that the jaw movement data of plural men preliminarily stored in the file 32 is read out and converted to images to be displayed on the display 41 and that a user selects jaw movement data regarded as similar to the dentition or residual ridge (the positions of cuspid apexes, for example) of the subject and as most suitable out of them.

(ii) Measurement point selecting process step 23b

As shown in FIG. 4A and FIG. 4B, a dentition configuration diagram (FIG. 4A), obtained by converting the dentition configuration data to an image, and a jaw movement state diagram (FIG. 4B), obtained by converting the jaw movement data in the basic state of jaw movement (at the intercuspal position) to an image, are displayed on the display 41 (S103).

Then cuspid apexes $P_{a1}$ to $P_{a8}$ are set for respective tooth buds 81 to 83, 91 to 93 of upper and lower dentitions 80, 90 in the dentition configuration diagram thus displayed. In this FIG. 4A there are adjacent teeth 91, 93 on either side of abutment tooth 92 on which a prosthesis is to be mounted, and pairing teeth 81 to 83 opposed thereto. The cuspid apexes may be extracted automatically, or, if they cannot be extracted automatically, the user may set them manually as observing the screen.

As shown in FIG. 4A and FIG. 4B, the three-dimensional configuration of the upper and lower dentitions 80, 90 is displayed on the left side of screen while the jaw movement state diagram at the intercuspal position on the right side of screen. In this example a cuspid apex of each tooth bud of the maxillary dentition is indicated by a point (a circle). The left screen (FIG. 4A) indicates the three-dimensional configuration of three pairs of left molar teeth located in the rectangular region R surrounded by the dashed line in the right screen.

Next, correspondence is made between the cuspid apexes existing in the both of the dentition configuration diagram (FIG. 4A) and jaw movement state diagram (FIG. 4B) (S104). Specifically, the user finds a cuspid apex in the dentition configuration diagram corresponding to that in the jaw movement state diagram and hits each of them by the mouse. Repeating this, the user produces some sets of cuspid apexes $P_{a1}$ and $P_{b1}$, $P_{a2}$ and $P_{b2}$, $P_{a3}$ and $P_{b3}$, $P_{a4}$ and $P_{b4}$, $P_{a4}$ and $P_{b5}$. After the sets of cuspid apexes are produced in this way, the following values are calculated for the object cuspid apexes in the jaw movement state diagram and for the object cuspid apexes in the dentition configuration diagram.

(iii) Center-of-gravity calculating process step 23c

As shown in FIG. 5A and FIG. 5B, calculated as to the three left molar teeth 81 to 83 located in the rectangular region R of the dashed line are the center of gravity $G_b$ of the object cuspid apexes $P_{b1}$ to $P_{b5}$ in the jaw movement state diagram and the center of gravity $G_a$ of the object cuspid apexes $P_{a1}$ to $P_{a5}$ in the dentition configuration diagram (S105). This calculation is made by obtaining the positions of these centers of gravity $G_a$, $G_b$ under such an assumption that the all object cuspid apexes $P_{a1}$ to $P_{a5}$, $P_{b1}$ to $P_{b5}$ have the same weight.

Namely, the center of gravity $G_a$ is obtained by calculating average values of respective X-, Y-, and Z-coordinates of the three-dimensional coordinate data of the cuspid apexes $P_{a1}$ to $P_{a5}$ in the dentition configuration diagram, while the center of gravity $G_b$ is obtained by calculating average values of respective X-,-Y, and Z-coordinates of the three-dimensional coordinate data of the cuspid apexes $P_{b1}$ to $P_{b5}$ in the jaw movement state diagram.

(iv) Moment axis calculating process step 23d

Figure 6B:
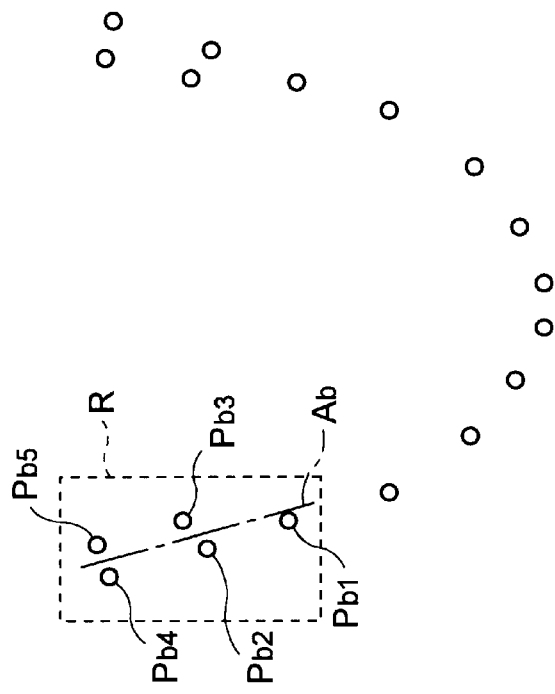
FIG. 6A and FIG. 6B are a plan view of dentition configuration and a plan view of jaw movement basic state, respectively, displayed on the display in the moment axis calculating step.
Figure 6A:
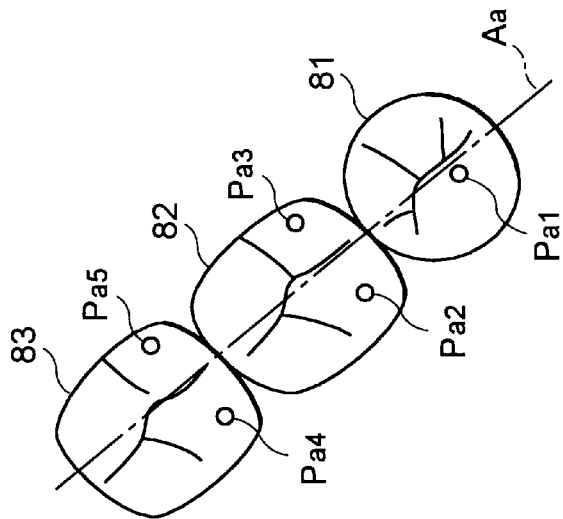
Figure 7B:
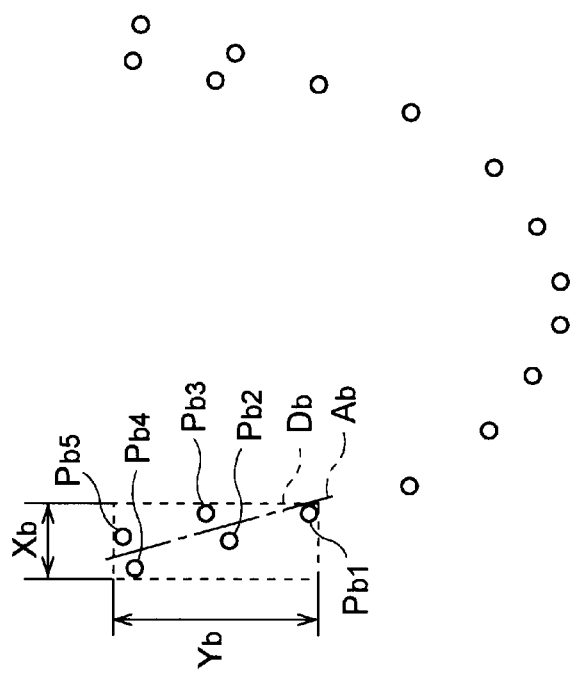
FIG. 7A and FIG. 7B are a plan view of dentition configuration and a plan view of jaw movement basic state, respectively, displayed on the display in the distribution area width calculating step.
Figure 7A:
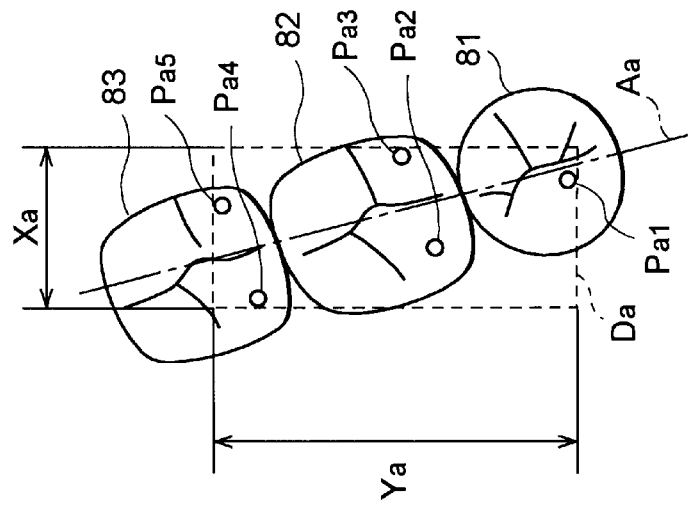
Figure 8A:
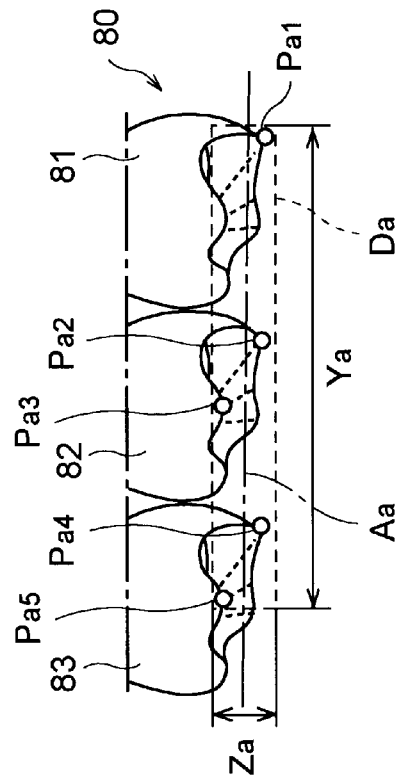
FIG. 8A and FIG. 8B are a side view of dentition configuration and a side view of jaw movement basic state, respectively, displayed on the display in the distribution area width calculating step.
Figure 8B:
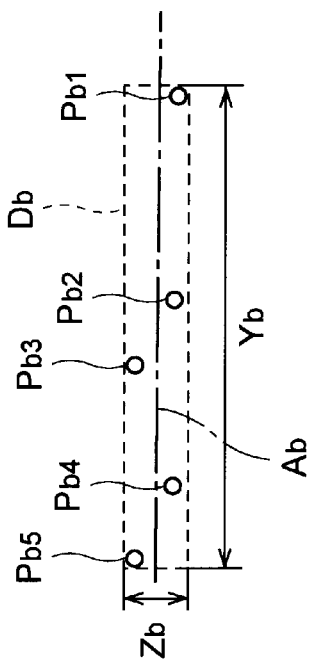

As shown in FIG. 6A and FIG. 6B, next calculated as to the three left molar teeth 81 to 83 located in the rectangular region R of the dashed line are a function of axis $A_b$ to minimize moments of the object cuspid apexes $P_{b1}$ to $P_{b5}$ in the jaw movement state diagram and a function of axis $A_a$ to minimize moments of the object cuspid apexes $P_{a1}$ to $P_{a5}$ in the dentition configuration diagram (S106).

Namely, the function of axis $A_a$ is obtained by the method of least squares from the three-dimensional coordinate data of the cuspid apexes $P_{a1}$ to $P_{a5}$ in the dentition configuration diagram and the function of axis $A_b$ by the method of least squares from the three-dimensional coordinate data of the cuspid apexes $P_{b1}$ to $P_{b5}$ in the jaw movement state diagram.

(v) Distribution area width calculating process step 23e

As shown in FIG. 7A, FIG. 7B, FIG. 8A, and FIG. 8B, first, the directions of axes $A_a$, $A_b$ to minimize the moments obtained as described above are aligned with each other (the axis $A_a$ in the dentition configuration diagram is aligned with the axis $A_b$ in the jaw movement state diagram), and a region $D_a$ or $D_b$ of a rectangular parallelepiped surrounding the cuspid apexes $P_{a1}$ to $P_{a5}$ or $P_{b1}$ to $P_{b5}$ of the three left molar teeth 81 to 83 is set in each diagram. Then obtained are X-, Y-, Z-axial widths $X_b$, $Y_b$, $Z_b$ of the region $D_b$ in the jaw movement state diagram and X-, Y-, Z-axial widths $X_a$, $Y_a$, $Z_a$ of the region $D_a$ in the dentition configuration diagram (S107).

In detail, the cuspid apexes $P_{a1}$ to $P_{a5}$ in the dentition configuration diagram are corrected so as to parallel the axis $A_a$ in the dentition configuration diagram with the axis $A_b$ in the jaw movement state diagram and the widths $X_a$, $Y_a$, $Z_a$ of distribution areas of the respective X-, Y-, Z-coordinates (each of which is a difference between the maximum and the minimum of each of the X-, Y-, Z-coordinates) are obtained from the three-dimensional coordinate data of the thus corrected cuspid apexes $P_{a1}$ to $P_{a5}$. Also, the widths $X_b$, $Y_b$, $Z_b$ of distribution areas of the respective X-, Y-, and Z-coordinates (each of which is a difference between the maximum and the minimum of each of the X-, Y-, Z-coordinates) are obtained from the three-dimensional coordinate data of the cuspid apexes $P_{b1}$ to $P_{b5}$ in the jaw movement state diagram.

(vi) Translation matrix calculating process step 23f

Obtained from the relation shown in FIG. 5A and FIG. 5B is a translation matrix T for matching the center of gravity $G_a$ in the dentition configuration diagram with the center of gravity $G_b$ in the jaw movement state diagram (S108). Namely, the difference between the three-dimensional coordinate data of the center of gravity $G_a$ and the three-dimensional coordinate data of the center of gravity $G_b$ corresponds to the translation matrix T.

(vii) Rotation matrix calculating process step 23g

Obtained from the relation shown in FIG. 6A and FIG. 6B is a rotation matrix R for matching the axis $A_a$ in the dentition configuration diagram with the axis $A_b$ in the jaw movement state diagram (S109). Namely, the difference between the function of axis $A_a$ and the function of axis $A_b$ (the difference of inclination) corresponds to the rotation matrix R.

(viii) Scaling matrix calculating process step 23h

Obtained from the relation shown in FIG. 7A, FIG. 7B, FIG. 8A, and FIG. 8B is a scaling matrix S for matching the distribution area widths $X_a$, $Y_a$, $Z_a$ of the corrected cuspid apexes $P_{a1}$ to $P_{a5}$ with the distribution area widths $X_b$, $Y_b$, $Z_b$ of the cuspid apexes $P_{b1}$ to $P_{b5}$ in the jaw movement state diagram (S110). Namely, ratios of respective distribution area widths $X_a$, $Y_a$, $Z_a$ and distribution area widths $X_b$, $Y_b$, $Z_b$ correspond to the scaling matrix S.

(iv) Dentition configuration data transforming process step 23i

A coordinate transformation matrix M for matching the dentition configuration diagram with the jaw movement state diagram by moving the former onto the latter can be obtained by the following equation using these matrices T, R, S. Translation, rotation, and scaling are carried out in the stated order.

(Coordinate transformation matrix) $M = T \times R \times S$

The relation between point Q after transformation and point P before transformation is expressed by the equation: $Q = P \times M$.

Then the dentition configuration data is transformed to coordinates on the coordinate system in the jaw movement basic state (at the intercuspal position), using the coordinate transformation matrix M comprised of the translation matrix T, rotation matrix R, and scaling matrix S as described, thereby obtaining the dentition configuration data (superimposed dentition configuration data) superimposed on the same coordinate system as that of the jaw movement data in the basic state (S111).

Although the measurement points of the jaw movement data in the basic state and the corresponding points of the dentition configuration data are measured and displayed in the different coordinate systems from each other, they are originally the same points and therefore, they must coincide with each other. Accordingly, when the dentition configuration data and jaw movement data originates from the same subject, they can match perfectly with each other. However, even in the case wherein the movement data is taken from the database as described above, they can match to some extent with each other if the positions of cuspid apexes are similar to each other.

(III) Simulation Process Step 24

(i) Superimposed diagram displaying process step 24a

Figure 9:
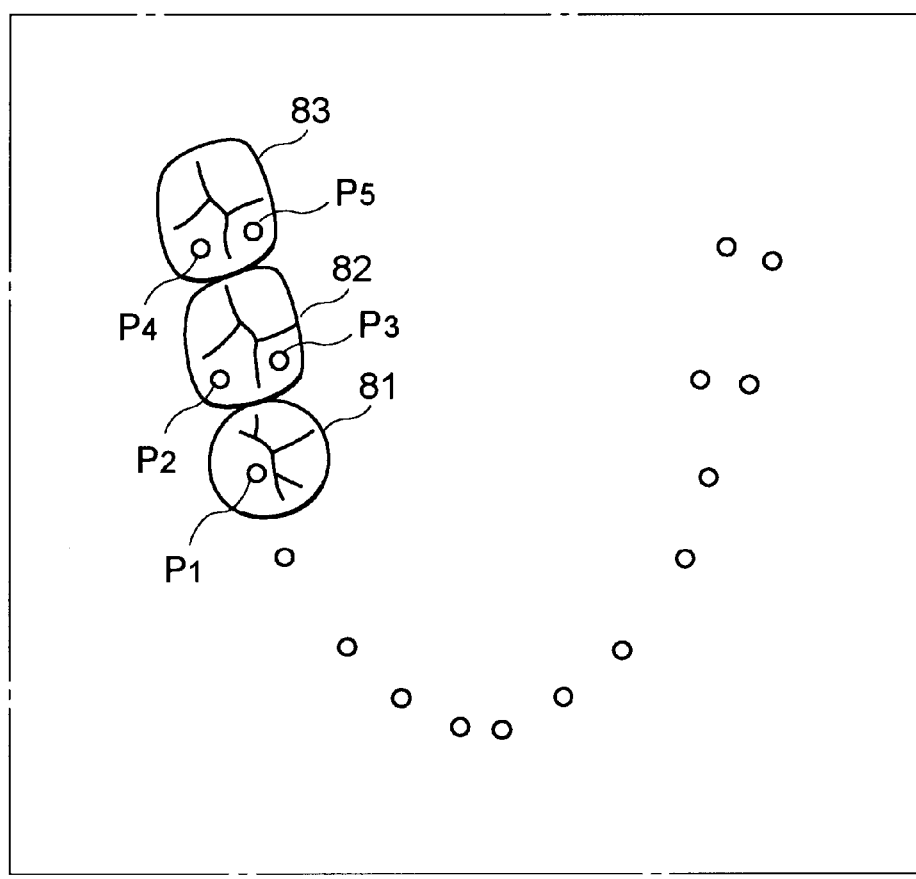
FIG. 9 is a superposed plan view in which a dentition configuration diagram is displayed as superimposed on a jaw movement state diagram on the display.

Since the superimposed dentition configuration data obtained by the matrix transformation as described above is superimposed on the same coordinate system as that of the jaw movement data in the basic state, a superimposed diagram can be displayed on the display 41 to show a superimposed image of the dentition configuration diagram obtained by converting the superimposed dentition configuration data to an image and the jaw movement state diagram obtained by converting the jaw movement data to an image, as shown in FIG. 9 (S112).

Figure 10A:
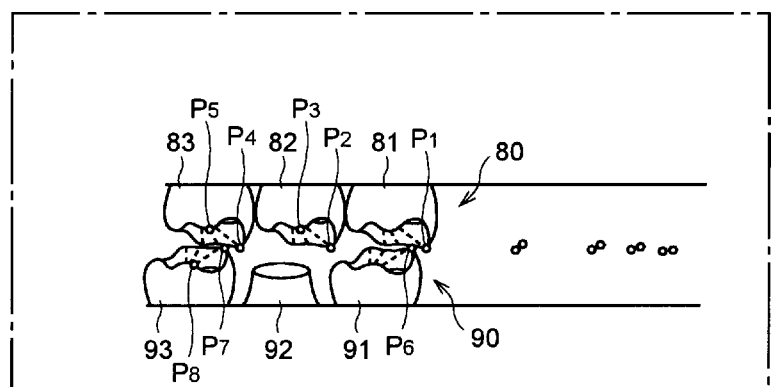
FIG. 10A, FIG. 10B, and FIG. 10C are superimposed side views in the jaw movement basic state (at the intercuspal position), in another jaw movement state (at an intermediate position), and in still another jaw movement state (at the maximum opening position), respectively.

Then the same matrix transformation as above is carried out for the lower dentition 90, whereby the dentition configuration diagram and jaw movement state diagram of the upper and lower dentitions 80, 90 can be displayed as superimposed on the display 41, as shown in FIG. 10A.

Figure 11:
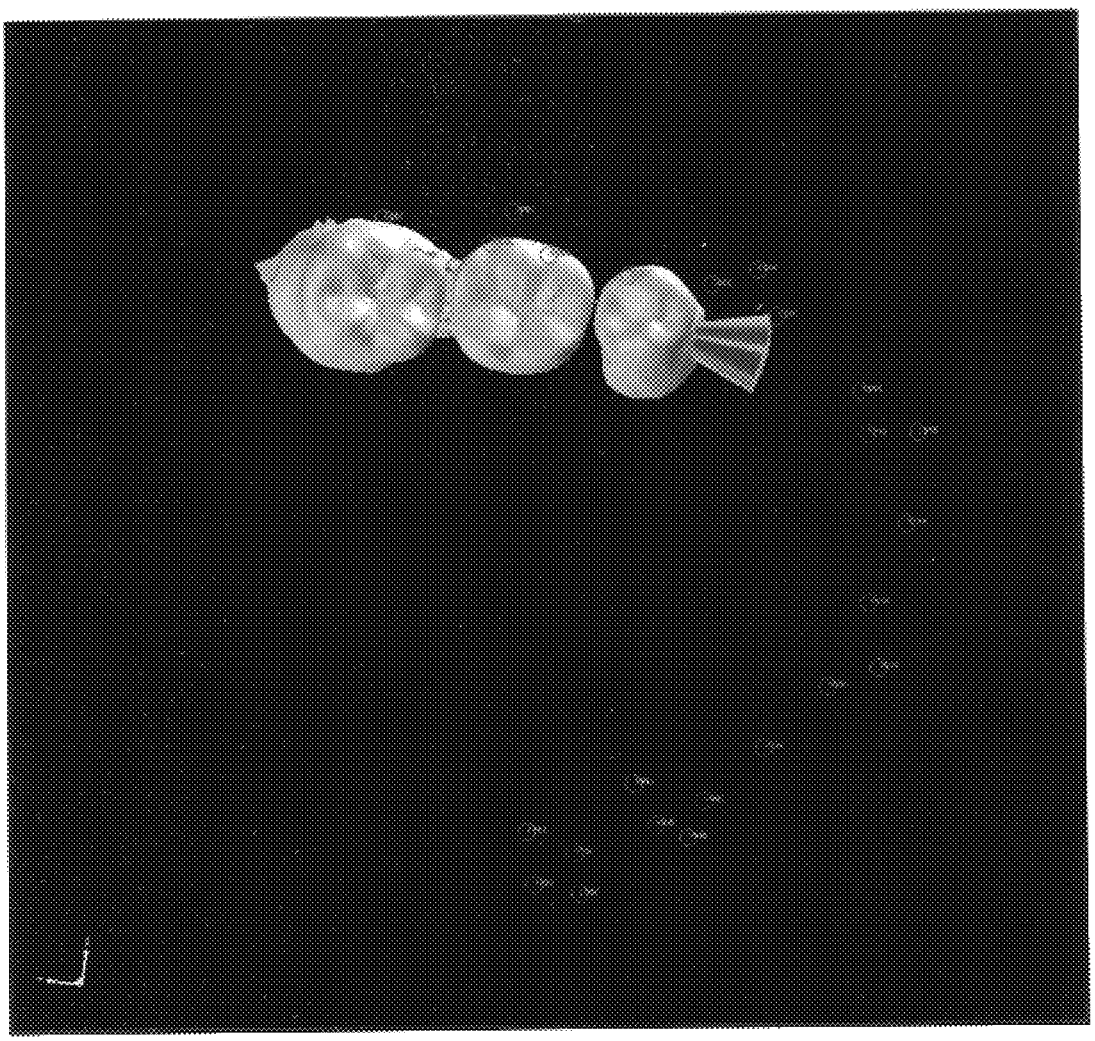
FIG. 11 is a photograph to show an example of the superimposed plan view in which the dentition configuration diagram is displayed as superimposed on the jaw movement state diagram on the display.

FIG. 11 shows a photograph of a superimposed plan view in which the dentition configuration diagram and jaw movement state diagram of the three left lower molar teeth are actually superimposedly displayed on the display in this way.

(ii) Jaw-movement-state dentition configuration data calculating process step 24b Since the superimposed dentition configuration data is superimposed on the same coordinate system as that of the jaw movement data in the basic state, dentition configuration data (superimposed dentition configuration data) after shifted into another jaw movement state can be calculated by a displacement matrix of jaw movement data in a shift from the basic state to another state (the difference of three-dimensional coordinate data between before and after the shift) (S113, S114).

Figure 10B:
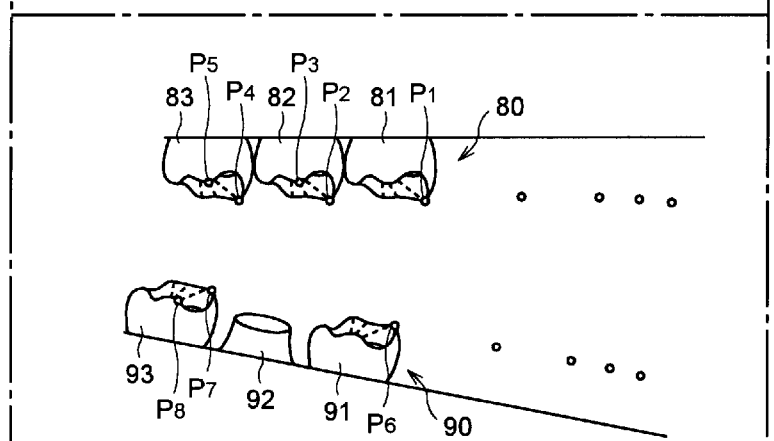
Figure 10C:
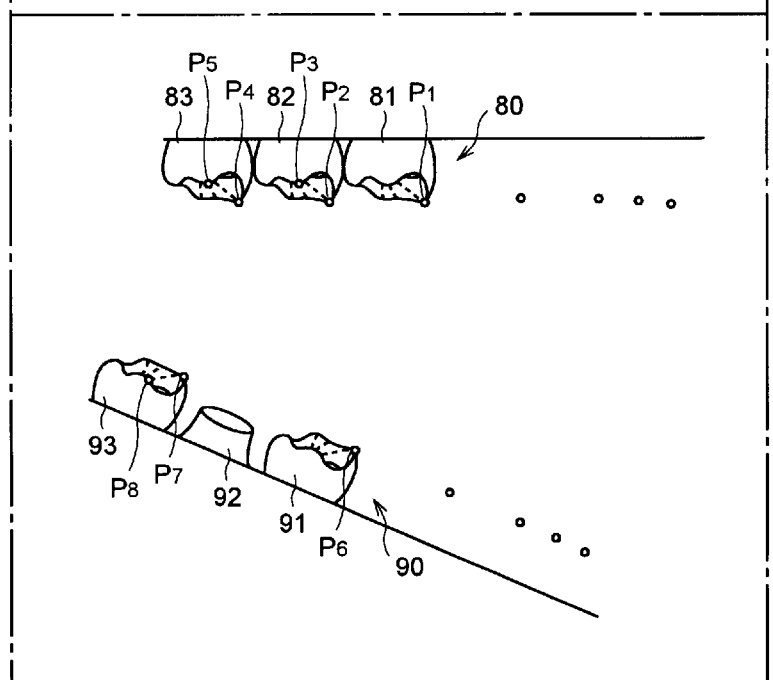

Therefore, using the superimposed dentition configuration data and jaw movement data in another jaw movement state thus calculated, the dentition configuration diagram and jaw movement state diagram can be superimposedly displayed on the display 41 in another jaw movement state (at an intermediate position as in FIG. 10B or at the maximum opening position as in FIG. 10C) as shown in FIG. 10B and FIG. 10C (S112).

Figure 12:
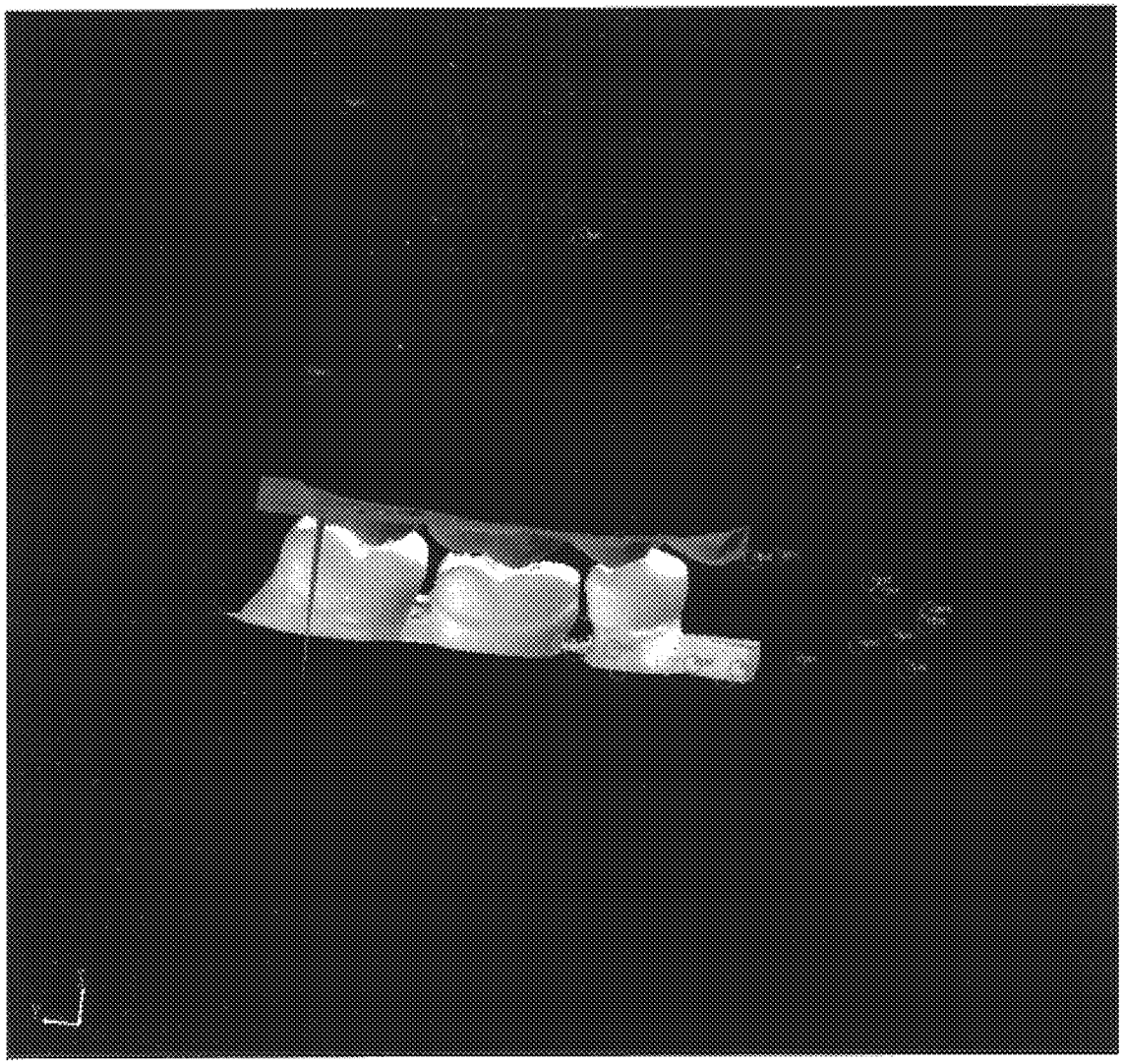
FIG. 12 is a photograph to show an example of the superimposed side view in the jaw movement basic state (at the intercuspal position)
Figure 13:
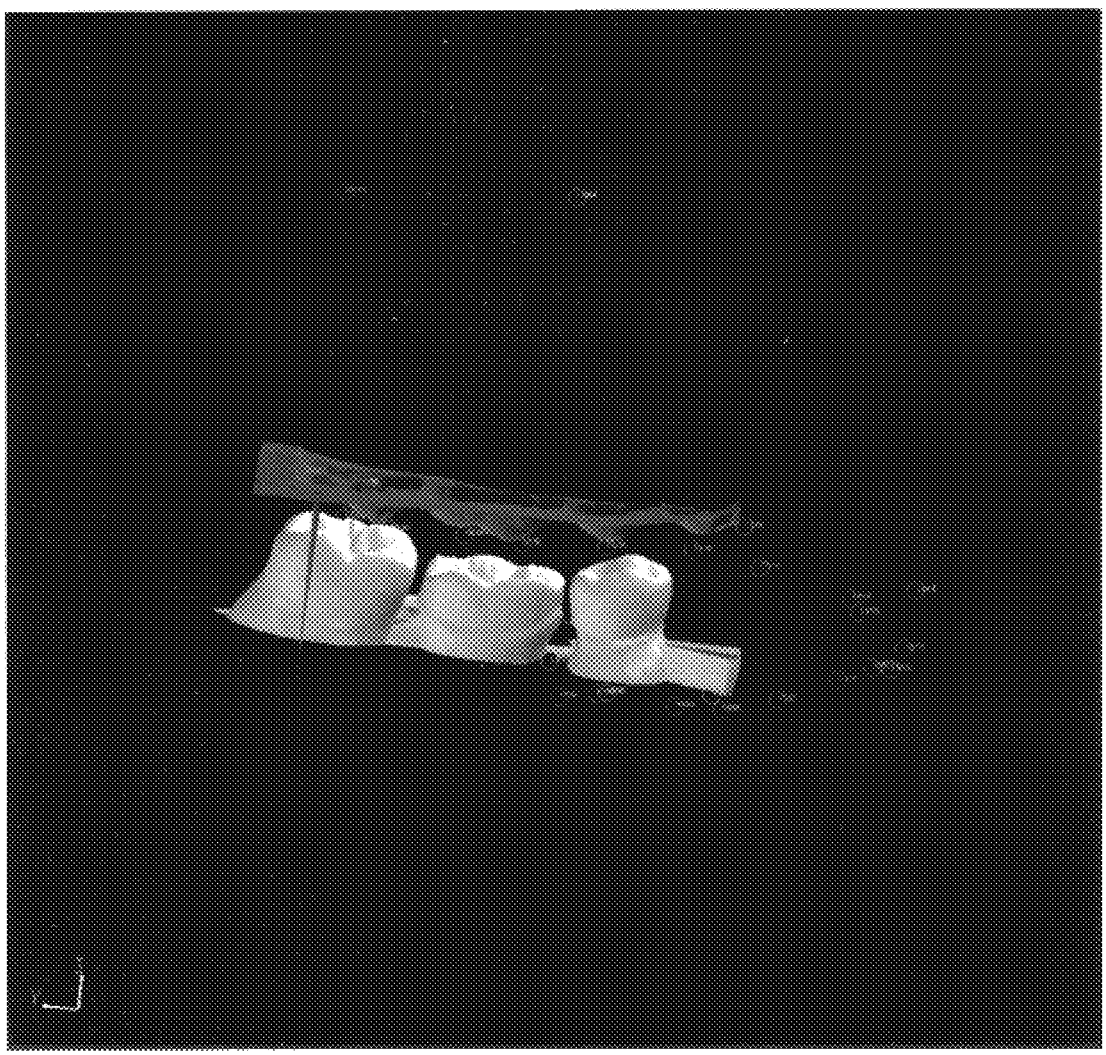
FIG. 13 is a photograph to show an example of the superimposed side view in another jaw movement state (at the intermediate position)
Figure 14:
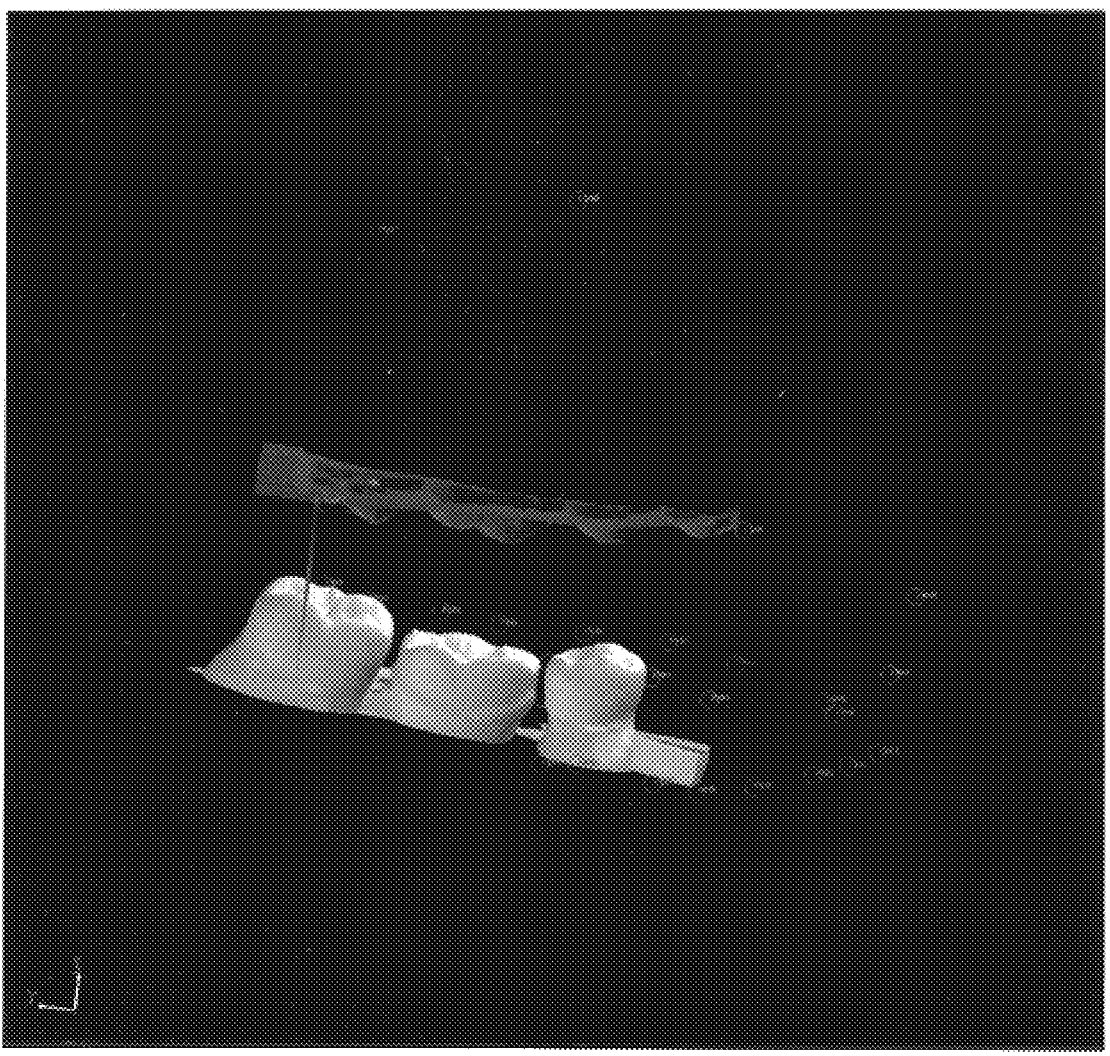
FIG. 14 is a photograph to show an example of the superimposed side view in still another jaw movement state (at the maximum opening position).

In this way, the superimposed dentition configuration data of the three left lower molar teeth is calculated in the jaw movement basic state (at the intercuspal position), in another jaw movement state (at the intermediate position), and in still another jaw movement state (at the maximum opening position), and they are actually displayed on the display. Photographs of superimposed side view in each state are shown in FIG. 12, FIG. 13, and FIG. 14, respectively.

Such dentition configuration diagrams in the plural jaw movement states are successively or simultaneously displayed on the display 41, whereby the dentition configuration data can be moved based on the jaw movement data. As a consequence thereof, the dentition configuration diagram to which motion is given as described moves to follow the loci of the jaw movement on the display 41. The jaw movement data is data obtained by sampling some states in one cycle of from the intercuspal position through the maximum opening position back to the intercuspal position, and the motion becomes smoother by carrying out the jaw movement simulation as connecting points by a curve, for example, such as the Bspline curve. Particularly, since the occluding condition of the maxilla and mandible can be observed more precisely in movement near the intercuspal position, a dental prosthesis can be designed so as to fit the subject more accurately.

If the three-dimensional dentition configuration data is displayed with surfaces provided thereon upon execution of such jaw movement simulation, a region of interference between the maxillary and mandibular dentitions can be found quickly on the screen, whereby presence or absence of interference can be checked without performing complex interference calculation. Further, in designing a dental prosthesis (for example, a single crown), the interference calculation of surface is carried out upon execution of movement to extract interfering regions on the single crown, and the interfering portions are corrected, whereby the occlusal surface of the single crown can be formed in a shape fitting the subject.

The preferred embodiment of the present invention was described above, but it is noted that the present invention is by no means limited to the above embodiment.

Namely, the above embodiment was arranged to measure the dentition configuration using the gypsum cast, but without having to be limited this method, the dentition configuration may be measured directly. In addition, the intercuspal position was employed as the basic state, but another state may be employed as the basic state. Further, the cuspid apexes were employed as the measurement points, but the measurement points may be any other characteristic, morphological points of tooth bud or any other marks attached to the dentition or residual ridge upon measurement.

As detailed above, the jaw movement simulation method and apparatus of the present invention is arranged to measure movement of the arbitrary number of measurement points such as the cuspid apexes of tooth bud with mastication of subject and to measure the three-dimensional configuration of jaw dentition of subject, thereby enabling easy simulation of the movement of jaw dentition with mastication, using these measurement data. This can achieve the simulation method and apparatus easy in data measurement and input and excellent in accuracy, which permits more precise designing of dental prosthesis.

Instead of actually measuring the loci of movement of subject's jaw, it is also possible to take the jaw movement data fitting the subject at that time out of the jaw movement data of plural men preliminarily stored in the database and to perform the jaw movement simulation using the jaw movement data thus taken, which can further decrease the load on the subject in data measurement.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 8-049762 (049762/1996) filed on Mar. 7, 1996 is hereby incorporated by reference.

What is claimed is:

1. A simulation method of jaw movement comprising:
   a superimposing process step of reading dentition configuration data out of a dentition configuration data file storing dentition configuration data indicating a three-dimensional configuration of a dentition or a residual ridge and reading jaw movement data out of a jaw movement data file storing jaw movement data indicating loci of movement of plural jaw movement measurement points on the dentition or the residual ridge with jaw movement, calculating a coordinate transformation matrix for matching a coordinate system of said dentition configuration data with a coordinate system in a jaw movement basic state in said jaw movement data, and transforming said dentition configuration data to coordinates on the coordinate system in said jaw movement basic state using the coordinate transformation matrix to obtain superimposed dentition configuration data; and a simulation process step of, based on said jaw movement data and said superimposed dentition configuration data, calculating superimposed dentition configuration data in another jaw movement state and superimposedly displaying a dentition configuration diagram obtained by converting said superimposed dentition configuration data to an image and a jaw movement state diagram obtained by converting said jaw movement data to an image.

2. The method according to claim 1, further comprising a dentition configuration measuring step of measuring a three-dimensional configuration of a dentition or a residual ridge of a subject to obtain dentition configuration data thereof and storing the dentition configuration data obtained in said dentition configuration data file.

3. The method according to claim 1, further comprising a jaw movement measuring step of measuring loci of movement of plural jaw movement measurement points on a dentition or a residual ridge with jaw movement of a subject to obtain jaw movement data thereof and storing the jaw movement data obtained in said jaw movement data file.

4. The method according to claim 1, wherein jaw movement data of plural men is stored in said jaw movement data file and jaw movement data about a dentition or a residual ridge similar to the dentition or the residual ridge of the subject is read out of said jaw movement data file as being selected from said jaw movement data of plural men.

5. The method according to claim 1, wherein said superimposing process step comprises:
   a step of reading the dentition configuration data out of the dentition configuration data file storing the dentition configuration data indicating the three-dimensional configuration of the dentition or the residual ridge and reading the jaw movement data out of the jaw movement data file storing the jaw movement data indicating the loci of movement of the plural jaw movement measurement points on the dentition or the residual ridge with jaw movement;

a step of displaying a dentition configuration diagram obtained by converting said dentition configuration data to an image and a jaw movement state diagram obtained by converting the jaw movement data in the jaw movement basic state to an image and selecting jaw movement measurement points in said jaw movement state diagram and dentition configuration measurement points corresponding thereto in said dentition configuration diagram;

a step of calculating a center of gravity of said dentition configuration measurement points and a center of gravity of said jaw movement measurement points;

a step of calculating a function of a dentition configuration moment axis to minimize moments of said dentition configuration measurement points and a function of a jaw movement moment axis to minimize moments of said jaw movement measurement points;

a step of correcting said dentition configuration measurement points so as to parallel said dentition configuration moment axis with said jaw movement moment axis to obtain corrected dentition configuration measurement points and calculating distribution area widths of respective three-dimensional coordinates of said corrected dentition configuration measurement points and distribution area widths of respective three-dimensional coordinates of said jaw movement measurement points;

a step of calculating a translation matrix for matching the center of gravity of said dentition configuration measurement points with the center of gravity of said jaw movement measurement points;

a step of calculating a rotation matrix for matching said dentition configuration moment axis with said jaw movement moment axis;

a step of calculating a scaling matrix for matching the distribution area widths of said corrected dentition configuration measurement points with the distribution area widths of said jaw movement measurement points; and a step of transforming said dentition configuration data to coordinates on the coordinate system in said jaw movement basic state using a coordinate transformation matrix comprised of said translation matrix, said rotation matrix, and said scaling matrix to obtain superimposed dentition configuration data.

6. A simulation apparatus of jaw movement comprising:

a storage device for storing a dentition configuration data file saving dentition configuration data indicating a three-dimensional configuration of a dentition or a residual ridge and a jaw movement data file saving jaw movement data indicating loci of movement of plural jaw movement measurement points on the dentition or the residual ridge with jaw movement;

an input device;

a display device;

a superimposing process section for reading the dentition configuration data out of said dentition configuration data file and the jaw movement data out of said jaw movement data file, respectively, calculating a coordinate transformation matrix for matching a coordinate system of said dentition configuration data with a coordinate system in a jaw movement basic state in said jaw movement data, and transforming said dentition configuration data to coordinates on the coordinate system in said jaw movement basic state using the coordinate transformation matrix to obtain superimposed dentition configuration data; and a simulation process section for, based on said jaw movement data and said superimposed dentition configuration data, calculating superimposed dentition configuration data in another jaw movement state and superimposedly displaying a dentition configuration diagram obtained by converting said superimposed dentition configuration data to an image and a jaw movement state diagram obtained by converting said jaw movement data to an image on said display device.

7. The apparatus according to claim 6, further comprising a dentition configuration measuring device for measuring a three-dimensional configuration of a dentition or a residual ridge of a subject to obtain dentition configuration data and storing the dentition configuration data obtained in said dentition configuration data file.

8. The apparatus according to claim 6, further comprising a jaw movement measuring device for measuring loci of movement of plural jaw movement measurement points on a dentition or a residual ridge with jaw movement of a subject to obtain jaw movement data and storing the jaw movement data obtained in said jaw movement data file.

9. The apparatus according to claim 6, wherein jaw movement data of plural men is stored in said jaw movement data file and said superimposing process section reads jaw movement data about a dentition or a residual ridge similar to the dentition or the residual ridge of the subject out of said jaw movement data file as selecting it out of said jaw movement data of plural men.

10. The apparatus according to claim 6, wherein said superimposing process section comprises:

a data reading process section for reading the dentition configuration data out of said dentition configuration data file and the jaw movement data out of said jaw movement data file, respectively:

a measurement point selecting process section for displaying a dentition configuration diagram obtained by converting said dentition configuration data to an image and a jaw movement state diagram obtained by converting the jaw movement data in the jaw movement basic state to an image on said display device and for accepting selection of jaw movement measurement points in said jaw movement state diagram and dentition configuration measurement points corresponding thereto in said dentition configuration diagram through said input device;

a center-of-gravity calculating process section for calculating a center of gravity of said dentition configuration measurement points and a center of gravity of said jaw movement measurement points;

a moment axis calculating process section for calculating a function of a dentition configuration moment axis to minimize moments of said dentition configuration measurement points and a function of a jaw movement moment axis to minimize moments of said jaw movement measurement points;

a distribution area calculating process section for correcting said dentition configuration measurement points so as to parallel said dentition configuration moment axis with said jaw movement moment axis to obtain corrected dentition configuration measurement points and for calculating distribution area widths of respective three-dimensional coordinates of said corrected dentition configuration measurement points and distribution area widths of respective three-dimensional coordinates of said jaw movement measurement points;

a translation matrix calculating process section for calculating a translation matrix for matching the center of gravity of said dentition configuration measurement points with the center of gravity of said jaw movement measurement points;

a rotation matrix calculating process section for calculating a rotation matrix for matching said dentition configuration moment axis with said jaw movement moment axis;

a scaling matrix calculating process section for calculating a scaling matrix for matching the distribution area widths of said corrected dentition configuration measurement points with the distribution area widths of said jaw movement measurement points; and a dentition configuration data transforming process section for transforming said dentition configuration data to coordinates on the coordinate system in said jaw movement basic state using a coordinate transformation matrix comprised of said translation matrix, said rotation matrix, and said scaling matrix to obtain superimposed dentition configuration data.

* * * * *